United States Patent [19]
Wands et al.

[11] Patent Number: 4,933,275
[45] Date of Patent: Jun. 12, 1990

[54] METHOD FOR THE DETECTION OF A POLYPEPTIDE SUBUNIT IN THE PRESENCE OF A QUATERNARY PROTEIN CONTAINING THE SUBUNIT

[75] Inventors: Jack R. Wands, Waban; Mehmet Ozturk, Boston, both of Mass.; Dominique Bellet, Paris, France

[73] Assignee: The General Hospital Corporation, Boston, Mass.

[21] Appl. No.: 791,114

[22] Filed: Oct. 24, 1985

[51] Int. Cl.$^5$ .................. G01N 33/535; G01N 37/577
[52] U.S. Cl. .................................... 435/7; 435/240.27; 435/810; 436/518; 436/540; 436/548; 436/814; 436/817; 436/818
[58] Field of Search ............. 435/7, 240, 810, 240.27; 530/387; 436/548, 817, 818, 814, 518, 540

[56] References Cited

U.S. PATENT DOCUMENTS

| | | | |
|---|---|---|---|
| 4,098,876 | 4/1978 | Piasio et al. | 424/1 |
| 4,138,214 | 2/1979 | Givner | 436/826 X |
| 4,289,747 | 9/1981 | Chu | 424/1 |
| 4,298,685 | 11/1981 | Parikh et al. | 435/7 |
| 4,343,896 | 8/1982 | Wolters et al. | 435/7 |
| 4,376,110 | 3/1983 | David et al. | 436/513 |
| 4,471,058 | 9/1984 | Smith et al. | 436/548 X |
| 4,496,658 | 1/1985 | Kondo et al. | 436/518 X |
| 4,565,687 | 1/1986 | Khazaeli et al. | 424/1.1 |

OTHER PUBLICATIONS

Cole et al., J. Clin. Endocrin., 58(6): 1200-1202, (1984).
Ehdich et al., Am. J. Rep. Immun. Microb., 8: 48-54, (1985).
Uotila et al., J. Immun. Meth., 42: 11-15, (1981).
Shimizu et al., Clin. Chem. 28(3): 546-547, (1982).
Mizuchi et al., J. Immunol. Meth. 74(1): 369-374, (1984).
Rugg et al., Clin. Chem. 32(10): 1844-1848, (1986).
Longhi et al., J. Immunol. Meth. 92(1): 89-95, (1986).
Bellet et al., J. Clin. Endocrinol. Metab. 63(6): 1319-1327, (1986).
Vaitukaitis et al, Am. J. Obstet. Gynecol., 113:751-758, (1972).
Pandian et al, Endocrinol., 107:1564-1571, (1980).
Matsuura et al, Endocrinol., 104:396-401, (1979).
Birken et al, Endocrinol., 110:1555-1563, (1982).
Armstrong et al, J. Clin. Endocrinol. Metab., 59:867-874, (1984).
Khazaeli et al, Endocrinol., 109:1290-1292, (1981).
Stuart et al., J. Endocr., 98:323-330, (1983).
Wang et al, Hybridoma, 1:293-302, (1982).
Bellet et al., Hybridoma, 1:218-219, (1982).
Bidart et al, J. Immunol., 134:457-464, (1985).
Bellet et al, Endocrinol., 115:330-336, (1984).
Cole et al, Endocrinol., 113:1176-1178, (1983).

(List continued on next page.)

Primary Examiner—Christine M. Nucker
Attorney, Agent, or Firm—Saidman, Sterne, Kessler & Goldstein

[57] ABSTRACT

A method for the determination of a free protein subunit of a quaternary protein in a sample, which comprises:
(a) contacting a sample with a first immunological binding partner which is or will be bound to a carrier, wherein the first immunological binding partner binds epitopic determinants bindable only on the free protein subunit;
(b) incubating the components of step (a) for a period of time and under conditions sufficient to form an immune complex between the free protein subunit, the first immunological binding partner, and the carrier;
(c) separating the carrier of step (b) from the sample;
(d) adding to the carrier of step (c), a detectably-labeled second immunological binding partner, wherein the second immunological binding partner binds epitopic determinants bindable on both the free protein subunit and the quaternary protein; and
(e) determining the detectably-labeled second immunological binding partner in the carrier or in liquid phase.

34 Claims, 3 Drawing Sheets

OTHER PUBLICATIONS

Nagelberg et al, *Cancer*, 55:1924–1930, (1985).
Hussa and Cole, "New Horizons in hCG Detection", *World Congress on Trophoblast Neoplasma*, Plenum Press, pp. 217–243, (1984).

Ashitaka et al., Endocrinol. Japon, 21:429–435, (1974).
Weintraub et al., *J. Clin. Invest.*, 52:3135–3142, (1973).
Blackman et al., J. Nat. Can. Inst., 65:81–93, (1980).
Hattori et al., Cancer, 46:355–361, (1980).
Cole et al., *J. Clin. Endocrin. Metabl,* 58: 1200–1202, (1984).

Vaitukaitis, *New Eng. J. Med.,* 301:324–326, (1979).
Tyrey, L., Sem. Oncol. 9:163–173, (1982).
Caraux, J. et al., J. Immunol 134: 835–840, (1985).
Light et al., *Lancet,* 1: 1284, (1983).
Skelly, D. S., *The Ligand Review,* 3(Supp.2): 4, (1981).
Hussa, R. O., *The Ligand Review,* 3(Supp.2):6–44, (1981).

Vaitukaitis, J. L., *The Ligand Review,* 3(Supp.2)45–48, (1981).
Tandem—Visual HCG Pregnancy Test, Hybritech Inc., San Diego, CA 92121.
Pregnospia, Organon Diagnostics, West Orange, NJ 07052.
Neo-Pregnosticon Duoclon, Organon Diagnostics, West Orange, NJ 07052.
Star beta–hCG RIA, Syncor International Corp., Sylmar, CA 91342.
Pregnastick Monoclonal Antibodies, Inc., Mountain View, CA 94043.
Model Serum HCG Assay, Monoclonal Antibodies, Inc., Mountain View, CA 94043.
Model Plus Urine hCG Assay, Monoclonal Anbibodies, Inc., Mountain View, CA 94043.
Beta–Neocept, Organon Diagnostics, West Orange, NJ 07052.
Ventrescreen hCG, Ventrex Laboratories Inc., Portland, ME 04103.

METHOD FOR THE DETECTION OF A POLYPEPTIDE SUBUNIT IN THE PRESENCE OF A QUATERNARY PROTEIN CONTAINING THE SUBUNIT

BACKGROUND OF THE INVENTION

1. Field of the Invention

The present invention relates to a method of detecting the presence of a free polypeptide subunit in the presence of protein which has the subunit as part of its quaternary structure.

2. Brief Description of the Background Art

The structure of proteins can be characterized at several levels of complexity. The primary structure of a protein refers to the sequence of amino acid residues which compose the covalent backbone of the polypeptide chain. The secondary structure of a polypeptide chain is its helically coiled conformation. The tertiary structure of a protein denotes the folded and highly compact conformation of the polypeptide chain. The quaternary structure of a protein results from the aggregation of separately synthesized polypeptide subunits.

Proteins which are composed of more than one polypeptide subunit are known as oligomeric proteins. Examples of oligomeric proteins are the glycoprotein hormones such as, for example, human chorionic gonadotropin; oxygen transport proteins such as hemoglobin; and enzymes such as lactate dehydrogenase.

The glycoprotein hormones in man which are of major medical significance include chorionic gonadotropin (hCG), luteinizing hormone (hLH), follicles-timulating hormone (hFSH), and thyroid-stimulating hormone (hTSH), hCG is synthesized by the placenta during pregnancy whereas the other hormones are synthesized by the anterior pituitary gland. All four of these hormones are structurally related. These hormones are dimeric, composed of two non-covalently associated subunits, denoted alpha and beta. The amino acid composition of the alpha subunit is common to all four hormones, while the beta-subunits, which confer biological specificity, are structurally unique. All of these beta-subunits show some degree of amino acid sequence homology. In man, beta-hCG and beta-hLH are the most closely related, with an amino acid sequence homology of 82%. The amino acid sequence homologies of the beta-subunits of the other glycoprotein hormones range from 25-40%. Of interest in comparing the structure of beta-hCG to beta-hLH is the presence in beta-hCG of a 24 amino acid carboxyterminal polypeptide extension (CTP) which is not present in beta-hLH.

The molecular heterogeneity of hCG and the presence of hCG-related glycoproteins in both normal and malignant tissues has caused major difficulties in studying the regulation of hCG synthesis during pregnancy and the presumed mechanism of hCG genomic derepression in normal and malignant non-trophoblastic cells. The measurement of biologically active hCG levels during pregnancy and the detection of its tumor specific altered forms as biochemical markers of tumor development require the production of highly specific antibodies for either the intact hormone, its subunits, or related forms. Characteristically, most polyvalent antisera directed against hCG cross-react with the other glycoprotein hormones and may not immunologically distinguish hCG from its subunits or related forms. Although the use of highly purified beta-hCG (Vaitukaitis et al., American Journal of Obstetrics and Gynecology, 113: 751 (1972)), chemical analogues of beta-hCG (Pandian et al., Endocrinology, 107: 1564 (1980)), or carboxy-terminal peptides (Matsuura et al., Endocrinology, 104: 396 (1979); Birken et al., Endocrinology, 110: 1555 (1982)) as immunogens may permit the generation of antisera that selectively detect hCG in the presence of hLH, such antisera have thus far been unable to distinguish free beta-hCG subunit from intact native hCG (Armstrong et al., Journal of Clinical Endocrinology and Metabolism, 59: 867 (1984)). Thus, the use of polyclonal antibodies in immunodiagnostic test systems has limitations for proteins such as hCG where there is a group or family of similar proteins with varying degrees of structural homology.

In recent years, considerable research has focused on the use of developing monoclonal antibodies via hybridoma fusion techniques in order to attain the desired specificity. For example, Khazaeli et al. (Endocrinology, 109: 1290 (1981)) reported the production of a monoclonal antibody specific for the beta-hCG subunit which showed conflicting degrees of cross-reactivity with hCG. When cross-reactivity was measured in an ELISA assay in which hCG was immobilized, the authors found a minimal cross-reactivity with hCG of about 2%. When cross-reactivity was measured using a double antibody radioimmunoassay in which radioiodinated beta-hCG competed with increasing concentrations of hCG, the authors state that the monoclonal antibody showed a 0.23% cross-reactivity with hCG.

In Stuart et al., Journal of Endocrinology, 98: 323 (1983), the authors studied the production of monoclonal antibodies to hCG and its subunits. Of the monoclonal antibodies characterized by the authors, one reacted only with intact hCG, and another recognized only the free beta-subunit of hCG.

In Wang et al., Hybridoma, 1: 293 (1982), the authors describe the production of two different hybridomas secreting monoclonal antibodies specific for beta-hCG and alpha-hCG.

David et al. (U.S. Pat. No. 4,376,110) discloses a two-site immunometric assay using monoclonal antibodies from two different clones such that the monoclonal antibodies derived from these clones have specificity for different epitopes of the antigen.

In Givner (U.S. Pat. No. 4,138,214), a method and device for detecting pregnancy is disclosed. The device concentrates a body fluid and detection occurs using a monoclonal antibody specific for the betasubunit of hCG.

None of these references discloses a method for detecting nanogram quantities of free beta-hCG subunit in the presence of microgram quantities of hCG, as is often encountered in clinical specimens.

SUMMARY OF THE INVENTION

Monoclonal antibodies are used to detect free polypeptide subunits of a quaternary protein in the presence of a quaternary protein containing the polypeptide subunit. By determining the ratio of free subunit to quaternary protein, it is possible to determine patient status with respect to certain neoplasms.

The concentration of free subunit in a sample is determined by contacting a sample with a first monoclonal antibody specific for epitopes accessible only on the free subunit, and with a second monoclonal antibody which binds epitopes on both the free protein subunit and the quaternary protein.

The concentration of quaternary protein can be determined by contacting the same or a separate aliquot of the sample with a third monoclonal antibody which is specific for epitopes present only on the intact quaternary protein molecule and said second monoclonal antibody which binds epitopes on both free protein subunit and quaternary protein.

Thus, the present invention provides a method for the determination of a free protein subunit of a quaternary protein in a sample, which comprises:

(a) contacting said sample with a first immunological binding partner which is or will be bound to a carrier, wherein said first immunological binding partner binds epitopic determinants bindable only on said free protein subunit;

(b) incubating the components of step (a) for a period of time and under conditions sufficient to form an immune complex between said free protein subunit, said first immunological binding partner, and said carrier;

(c) separating said carrier of step (b) from said sample;

(d) adding to said carrier of step (c) a detectably-labeled second immunological binding partner, wherein said second immunological binding partner binds epitopic determinants bindable on both said free protein subunit and said quaternary protein; and (e) determining the detectably-labeled second immunological binding partner in said carrier or remaining in solution.

BRIEF DESCRIPTION OF THE PREFERRED EMBODIMENTS

In the method according to the invention, a sample containing both free protein subunit of a quaternary protein, and intact quaternary protein of which the protein subunit is a part, is contacted with a first immunological binding partner, a second immunological binding partner, and a third immunological binding partner. The first and second binding partners react with different regions of the protein subunit such that both partners can bind to the protein subunit. The first binding partner is usually an antibody. The second binding partner is also usually an antibody which is detectably labeled. The third binding partner is usually an antibody and may or may not be labeled depending upon which embodiment of the invention is applied.

Figure 1:
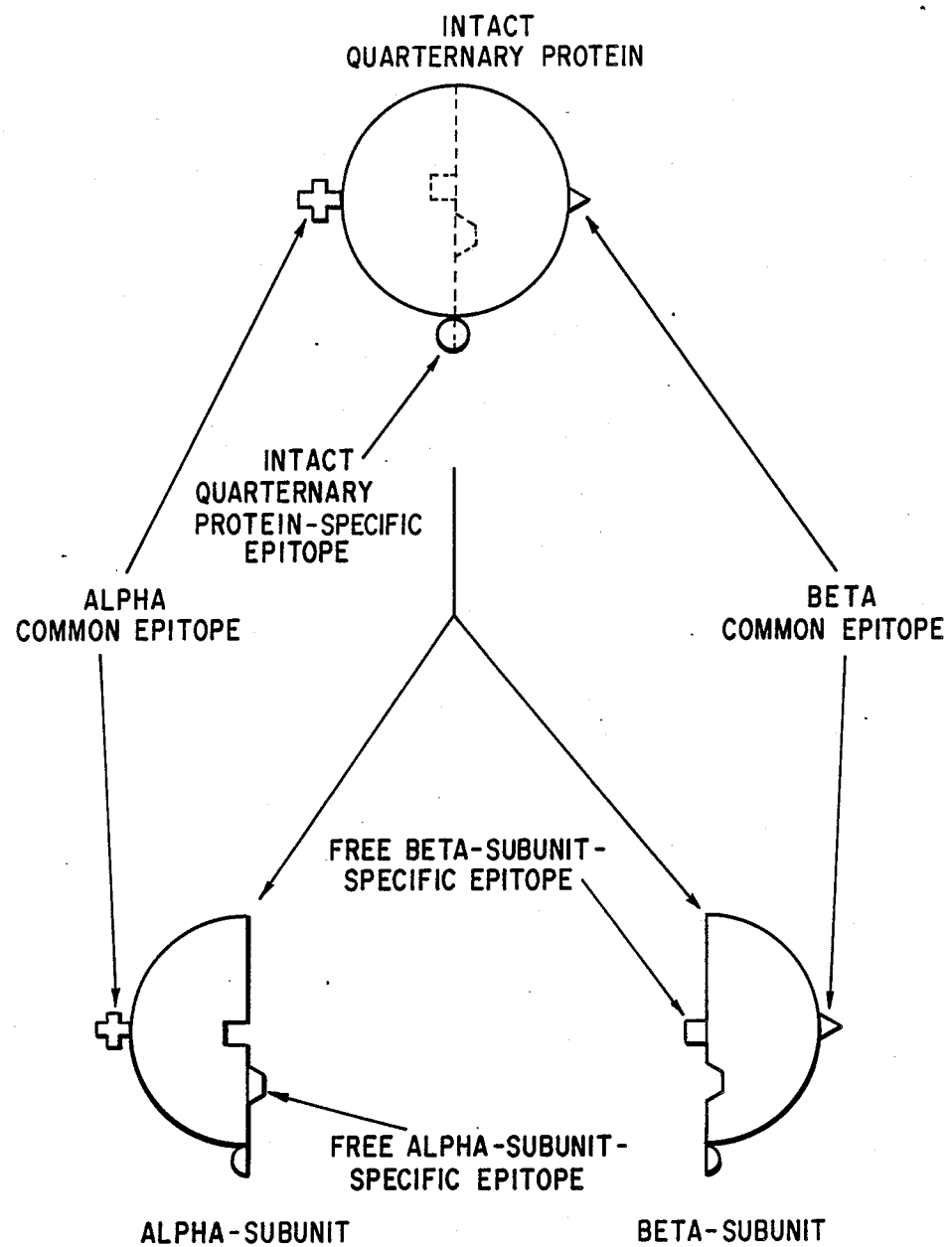
FIG. 1: Schematic representation of the arrangement of the epitopes of a polypeptide subunit of a quaternary protein, and a quaternary protein, detectable by the invention.

FIG. 1 is a schematic representation illustrating the arrangement of the epitopes of a quaternary protein detectable by the invention. For simplicity, the figure shows a quaternary protein consisting of only two subunits (alpha and beta), although quaternary proteins having more subunits would also be detectable according to the method of the invention.

As shown on the drawing, the quaternary protein specific epitope (small circle) is present only when the alpha and beta subunits are in association. Thus, an antibody to this epitope could not bind to either the free alpha or beta subunits.

The free beta subunit specific epitope (small square) is only accessible to an antibody with specificity for this epitope when the beta-subunit is not part of the quaternary protein.

The presence of an epitope common to both the free beta subunit and the quaternary protein is also shown (small triangle). The accessibility of this epitope enables it to bind antibody whether the beta subunit is free, or part of, the quaternary protein.

The free alpha-subunit epitope (half-hexagon) is only accessible to an antibody with specificity for this epitope when the alpha-subunit is not part of the quaternary protein.

An epitope common to the alpha-subunit when free, or as part of the intact quaternary protein, is also shown (cross). This epitope can be bound by antibody whether the alpha-subunit is free, or part of, the quaternary protein.

In a first embodiment, a sample is incubated with a first binding partner which is specific for epitopic determinants on the protein subunit which are not accessible when the protein subunit is part of the intact quaternary protein. Incubation is continued for a period of time sufficient to allow the protein subunit and the first binding partner to react. After the first incubation, the complex containing the first binding partner is removed from the sample and is placed in contact with the detectably labeled second binding partner. The second binding partner reacts with epitopic determinants present on the protein subunit when the protein subunit is free or as part of the intact quaternary protein. Incubation is allowed to occur for a time sufficient to allow binding to occur between the protein subunit (now complexed) and the second binding partner. After the second incubation, the reaction mixture is washed to remove any non-specifically bound labeled second binding partner and the amount of labeled second binding partner bound to the free protein subunit or remaining in the liquid phase is then measured.

In a second embodiment, the sample is first incubated with the third immunological binding partner which is specific for an epitope present on the intact quaternary protein. Incubation is continued for a period of time sufficient to allow intact quaternary protein containing the protein subunit in the sample and the complex containing the third binding partner to react. After incubation, the third binding partner is removed from the sample and the bound intact quaternary protein is placed in contact with detectably labeled second immunological binding partner. After a second incubation to allow the second immunological binding partner to bind to the intact (complexed) quaternary protein, the amount of labeled second binding partner bound to the quaternary protein or remaining in the liquid phase is then measured.

It should be understood that intact quaternary protein can also be detected using other combinations of different immunological binding partners. For instance, intact quaternary protein can be detected by first incubating the sample with an immunological binding partner which binds epitopic determinants accessible on one of the subunits when the subunit is part of the intact quaternary protein. Incubation is continued for a period of time sufficient to allow intact quaternary protein containing the subunit in the sample and the complex containing the immunological binding partner to react. After incubation, the immunological binding partner is removed from the sample and the bound protein is placed in contact with a detectably labeled immunological binding partner that reacts with epitopes accessible on the other subunit of the intact quaternary protein. After a second incubation to allow the detectably labeled immunological binding partner to react with the other subunit of intact (complexed) quaternary protein, the amount of labeled binding partner bound to the quaternary protein or remaining in the liquid phase is measured. An example of a commercially available kit for measuring intact hCG in this manner is the Tandem-hCG$^R$ kit sold by Hybritech (San Diego, CA.).

By the term "will be bound" it is meant that the first immunological binding partner is not initially bound to the carrier. Instead, the first immunological binding partner reacts with the epitope for which it is specific prior to being bound to the carrier. Examples of immunological assays wherein immune complexes are formed prior to binding to a carrier are Chu (U.S. Pat. No. 4,289,747), Wolters et al. (U.S. Pat No. 4,343,896), Parikh, et al. (U.S. Pat. No. 4,298,685), and Gallati, et al (United Kingdom Patent Application GB 2,074,727A).

By comparing the amount of free protein subunit present, as determined in the first embodiment, to the amount of intact quaternary protein containing the protein subunit present in the sample, according to the method of the second or third embodiment, it is possible to determine the percentage of free subunit present relative to the amount of total intact quaternary protein present.

The specific concentrations of first, second, and third immunological binding partners, the temperature and time of incubation, as well as other assay conditions, can be varied depending on such factors as the concentration of the antigen in the sample, the nature of the sample, and the like. Those skilled in the art will be able to determine operative and optimal assay conditions for each determination while employing routine experimentation. For example, the immunoassay may be run at 4–45° C., preferably at 26° C., and each incubation step may be as long as 72 hours.

Other steps such as washing, stirring, shaking, filtering, or pre-assay extraction of protein subunit or quaternary protein and the like may, of course, be added to the assays, as may be desired or necessary for a particular situation. There are many carriers to which the immunological binding partners can be bound and which can be used in the present invention. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding the immunological binding partners, or will be able to ascertain such, using routine experimentation.

Depending on the particular embodiment of the invention, one or more of the immunological binding partners will be coupled with a detectable label such as an enzyme, radioactive isotope, fluorescent compound, chemiluminescent compound, or bioluminescent compound.

Those of ordinary skill in the art will know of other suitable labels for binding to the second partner, or will be able to ascertain such using experimentation. Furthermore, the binding of these labels to the immunological binding partner can be done using standard techniques common to those of ordinary skill in the art. One of the ways in which the immunological binding partner in the immunoassay can be detectably labeled is by linking this binding partner to an enzyme. This enzyme, in turn, when later exposed to its substrate will react to the substrate in such a manner as to produce a chemical moiety which can be detected, as, for example, spectrophotometric or fluoremetric means. Examples of enzymes that can be used to detectably label are malate dehydrogenase, staphylococcal nuclease, delta5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

The presence of an immunological binding partner can also be detected by labeling the immunological binding partner with a radioactive isotope. The presence of the radioactive isotope could then be determined by such means as the use of a gamma counter or a scintillation counter. Isotopes which are particularly useful are $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, $^{75}Se$, and $^{152}Eu$.

It is also possible to detect the presence of the immunological binding partner by labeling the binding partner with a fluorescent compound. When the fluorescently labeled binding partner is exposed to light of the proper wavelength, its presence can then be detected due to fluorescence of the dye. Among the most important fluorescent labeling compounds are fluorescein isothiocyanate, rhodamine, phycoerythrin, phycocyanin, allophycocyanin, o-phthaldehyde, and fluorescamine.

Another way in which the immunological binding partner can be detectably labeled is by coupling it to a chemiluminescent compound. The presence of the chemiluminescent-tagged immunological binding partner is then determined by detecting the presence of luminescence that arises during the course of a chemical reaction. Examples of particularly useful chemiluminescent labeling compounds are luminol, isoluminol, aromatic-acridinium ester, imidazole, acridinium salt, and oxalate ester.

Likewise, a bioluminescent compound may also be used to label the immunological binding partner. Bioluminescence is a special type of chemiluminescence which is found in biological systems and in which a catalytic protein increases the efficiency of the chemiluminescent reaction. The presence of a bioluminescent binding partner would be determined by detecting the presence of luminescence. Important bioluminescent compounds for purposes of labeling are luciferin, luciferase, and aequorin.

For purposes of the invention, the substance which is being detected by the immunoassay may be present in biological fluids and tissues, as well as samples derived from environmental and ecological sources.

Any sample containing a detectable yet unknown amount of free protein subunit of a quaternary protein can be used. Normally, the sample is a liquid (such as, for example, urine, saliva, cerebrospinal fluid, blood, serum and the like) or a solid or semi-solid (such as, for example, tissues, feces, and the like).

The term "epitope" as used in this invention is meant to include any determinant responsible for specific interaction with an antibody molecule. Epitopic determinants usually consist of chemically active surface groupings of molecules such as amino acids or sugar side chains and have specific three dimensional structural characteristics as well as specific charge characteristics.

Monoclonal antibodies, when used in the present invention, can be produced in various ways using techniques well understood by those having ordinary skill in the art and will not be repeated here. Details of these techniques are described in such books as *Monoclonal Antibodies-Hybridomas: A New Dimension in Biological Analysis*, edited by Roger H. Kennett et al., published by Plenum Press (1980).

For example, additional hybridomas to those specifically disclosed in the invention, which produce monoclonal antibodies which enable the detection of free beta-hCG subunit in the presence of hCG can be easily produced and isolated with minimal screening.

Hybridomas producing monoclonal antibodies specific for epitopes which are found on the free beta-hCG subunit, but not on hCG, are most effectively produced by first immunizing an animal from which hybridomas can be produced such as, for example, a Balb/c mouse, with initial subcutaneous injections of free beta-hCG subunit and/or carboxyterminal peptide/tetanus toxoid in Freund's adjuvant followed by booster injections of beta-hCG subunit within a few days of cell fusion. The fusion can be carried out using any of the techniques commonly known to those of ordinary skill in the art. The screening of the hybridomas to determine which ones are producing monoclonal antibodies specific for the free beta subunit of hCG is straightforward and can be done either in a standard Elisa or RIA format. For example, in an RIA screening format the culture supernatant, or ascites fluid from a hybridoma producing monoclonal antibody is reacted separately with $^{125}$I-[beta-hCG], $^{125}$I-[hCG], and $^{125}$I-[alpha-hCG]. If the monoclonal antibody reacts with the $^{125}$I-[beta-hCG], but not the $^{125}$I-[hCG] or $^{125}$I[alpha-hCG], then the monoclonal antibody is specific for the free beta-hCG subunit.

Hybridomas secreting monoclonal antibody reactive with epitopes present on hCG, but not on free subunits of hCG, are produced by immunizing an acceptable animal as described above, except that the immunogen is native intact hCG. In this instance, the determination of which hybridomas are producing a monoclonal antibody of the desired specificity is done similarly as described above except that the desired monoclonal antibodies would be those which react with $^{125}$I-[hCG], but not $^{125}$I-[beta-hCG] or 125I-[alpha-hCG] in the RIA.

Hybridomas secreting monoclonal antibiodies reactive with epitopes present on alpha and beta-hCG when found as free subunits or as part of intact quaternary hCG would also be produced by immunizing an acceptable animal with native intact hCG. To determine which hybridomas are producing monoclonal antibodies of the desired specificity screening can be done as described above. The desired monoclonal antibodies would react with $^{125}$I-[alpha-hCG], $^{125}$I-[beta-hCG], and $^{125}$I-[hCG].

Production of hybridomas secreting monoclonal antibodies specific for epitopes found on the free alpha-hCG subunit, but not on hCG, can be produced similarly as described above, except that the immunogen used is the free alpha-hCG subunit. The determination of which hybridomas are producing monoclonal antibodies of the desired specificity is done as described above, except that the desired monoclonal antibody would react with $^{125}$I-[alpha-hCG], but not $^{125}$I-[hCG] of $^{125}$I-[beta-hCG].

Hybridomas secreting monoclonal antibodies which react with epitopes common to the free beta-hCG subunit and hCG can be produced using either of the immunization protocols and immunogens described above. The procedure described for production of hybridomas secreting monoclonal antibodies specific for the free beta-hCG subunit is preferred since these immunogens will not result in the generation of hybridomas producing monoclonal antibodies reactive with free alpha-hCG subunits. In this case, monoclonal antibodies of the desired specificity are determined by their reactivity with $^{125}$I-[beta-hCG] and $^{125}$I-[hCG], but not $^{125}$I-[alpha-hCG].

Hybridomas producing monoclonal antibodies specific for epitopes common to the free alpha-hCG subunit and hCG can be produced by immunization with either free alpha-hCG subunit or hCG. Monoclonals of the desired specificity, when screened in the RIA described above, react with $^{125}$-I[alpha-hCG] and $^{125}$I-[hCG], but not $^{125}$I-[beta-hCG].

Among the substances which can be detected using the invention are hormones, enzymes, inflammatory proteins, and, more generally, globular proteins with a molecular weight greater than $5.0 \times 10^3$ daltons.

Hormones are substances that act to inhibit or excite metabolic activities. Examples of hormones of considerable interest are those associated with reproduction, such as human choriogonadotropin, luteinizing hormone, and follicle-stimulating hormone, as well as hormones associated with metabolism such as thyroid-stimulating hormone and the like.

Enzymes are protein molecules which catalyze biochemical reactions. Enzymes are so significant in maintaining a homeostatic environment that they effectively represent intermediate metabolism within the organism. Changes in the concentration of enzymes which are associated with certain biochemical pathways can be of valuable diagnostic significance in evaluating a disease state. Examples of enzymes of significance are most protein kinases, creatinine phosphokinase, lactate dehydrogenase, C reactive protein (CRP), serum amyloid P component (SAP), alpha-2 macroglobulin, and the like.

The materials for use in the assay of the invention are ideally suited for the preparation of a kit. Such a kit may comprise a carrier means being compartmentalized to receive in close confinement one or more container means such as vials, tubes, and the like, each of said container means comprising one of the separate elements to be used in the method.

For example, one of the said container means may comprise a first monoclonal antibody bound to a carrier. A second container may comprise soluble, detectably-labeled second monoclonal antibody, in lyophilized form or in solution. The carrier means may also contain a third container means comprising a detectably-labeled third monoclonal antibody in lyophilized form or in solution.

In addition, the carrier means may also contain a plurality of containers each of which comprises different, predetermined amounts of a known antigen. These latter containers can then be used to prepare a standard curve into which can be interpolated the results obtained from the sample containing the unknown amount of antigen.

Certain monoclonal antibodies or substantial immunological equivalents thereof can be utilized in applying the present assay to hCG. A first monoclonal antibody, hereinafter FBT10, is obtained from, or has the identifying characteristics of, an antibody obtained from cell line I-488. A second monoclonal antibody, hereinafter referred to as FBT11, is obtained from, or has the identifying characteristics of, an antibody obtained from cell line I-489. A third monoclonal antibody, hereinafter referred to as HT-13, is obtained from, or has the identifying characteristic of, an antibody obtained from cell line I-490. A fourth monoclonal antibody, hereinafter referred to as AHT20, is obtained from, or has the identifying characteristics of, antibody obtained from cell line I-491. These cell lines have been deposited, on Oct. 3, 1985, at the Collection National de Cultures de Micro-Organisms (CNCM), Institut Pasteur, 25 Rue de Docteur Roux, 75724 Paris, France. The identifying numbers of each of these cell lines (I-488 to I-491) are the accession numbers of the depository.

A fifth monoclonal antibody, hereinafter referred to as C8, is obtained from, or has the identifying characteristics of, an antibody obtained from cell line Z.

These monoclonal antibodies demonstrate specificity to unique epitopes on hCG and free alpha- or beta-hCG subunit. The monoclonal antibody C8 is directed toward a conformationally-specific antigenic determinant on hCG which is specific for the native form of the hormone, but not its subunits. Monoclonal antibody FBT11 is directed toward an epitope on the free beta-hCG subunit which is not accessible on native hCG for binding this monoclonal antibody. On the other hand, FBT10 binds an epitopic determinant which is present on the beta subunit of hCG when the subunit is free or in association with intact quaternary hCG. Monoclonal antibody AHT20 is directed to an epitope on the free alpha-subunit which is not accessible to antibody binding when the alpha-subunit is part of the intact quaternary protein. HT13 is a monoclonal antibody that recognizes an epitope on the alpha-subunit and beta-subunit when these subunits are free or are part of the intact quaternary protein. The high sensitivity and specificity of these monoclonal antibodies enable the use of immunoassays to measure hCG in its native form or the free alpha- or beta-hCG subunit in the presence of excess hCG. These immunoassays are particularly useful in studying the production of free alpha- or beta-hCG during normal pregnancy.

The method of the invention overcomes major problems in the specific immunological detection of hCG or its subunits in biological fluids. The structural homology between the glycoprotein hormones, particularly between hCG and hLH, has resulted in the fact that conventional polyclonal antisera produced thus far against hCG cross-react with hLH. This cross reactivity may be reduced somewhat by generating antisera to free beta-hCG subunit, its chemical analogues, or carboxyterminal peptides as immunogens. Although this approach has permitted substantial progress in recent years in the production of more hCG specific antisera, and has partially resolved some of the problems of cross-reactivity between the various glycoprotein hormones, other concerns have been raised. For example, these antisera have suffered from a lack of specificity between hCG and its related products such as, for example, free beta-hCG subunit and the carboxyterminal peptides. Such related products of hCG are detectable in sera or urine during pregnancy, tumors with trophoblastic elements, or in cancer patients with ectopic production. Furthermore, even the use of free beta-hCG subunit or CTP as immunogens leads to the production of antisera which recognize better the hCG related products than hCG itself. Thus, the use of polyclonal antibodies in immunoassays has significant limitations for antigens such as hCG where there is a group or family of glycoprotein hormones with varying degrees of structural homology. Immunoassays utilizing monoclonal antibodies with a specificity of those disclosed in the invention do not have the disadvantages found in prior art immunoassays.

More importantly, monoclonal antibodies having such specificity enable the detection of certain neoplasms wherein the production of excess amounts of free alpha- or beta-hCG subunit is clinically significant. For example, the diagnostic capability of these monoclonal antibodies can be used to distinguish between hydatiform mole and choriocarcinoma development from normal pregnancy where increased production of free alpha- or beta-hCG subunit has been reported.

Additionally, monoclonal antibodies of this specificity can be used to detect the presence of cross-reacting components or contaminants in highly purified hormone standards.

Having now generally described this invention, the same will be better understood by reference to certain specific examples which are incorporated herein for purposes of illustration only and are not intended to be limiting of the invention unless otherwise specified.

EXAMPLE 1

Assay for Free Beta-hCG Subunit in the Presence of hCG

A. Production of Monoclonal Antibodies

Purified hCG (CR-123), alpha-hCG (CR-123), and beta-hCG (CR-123-B-II-3) were obtained from the Center for Population Research, NICHHD, National Institutes of Health. hFSH (hFSH-3), hLH (hLH-I-3), hTSH (hTSH-I-5), beta-hTSH (Batch No. 2), beta-hFSH (Batch No. 2), and beta-hLH (Batch No. 3) were supplied by the National Hormone and Pituitary Program, NIADDKD, National Institutes of Health. The $^{125}$I-[hCG], $^{125}$I-[hFSH], and $^{125}$I-[beta-hCG] hormones were obtained from Commisariat a l'Energie Atomique (France).

Three immunization procedures were used for the generation of several libraries of monoclonal antibodies. The production of monoclonal antibodies have been previously described (Bellet et al., Hybridoma, 1: 218 (1982)). Antibody C8 was produced by immunization of Balb/C mice with native hCG (U.C.B., Bruxelles, Belgium). In brief, the immunization involved a subcutaneous injection of 25 ug hCG in Freund's complete adjuvant (FCA) followed by subcutaneous injections of 25 ug and 50 ug hCG, respectively, 36 days and 85 days later. The cell fusion was performed on day 253. Prior to cell fusion the animal was boosted with both an intraperitoneal and intravenous injection of 100 ug hCG on days 4, 3 (intrapertioneal), and 1 (intravenous) before fusion. Cell fusions were performed by incubating $10^8$ SP2/0 Ag14 myeloma cells with $5 \times 10^8$ spleen cells in 50% polyethylene glycol (molecular weight, 1,000).

Monoclonal antibodies designated FBT10 and FBT11 were produced by an immunization procedure which employed the use of both beta-hCG and carboxy-terminal peptide with tetanus toxoid (CTP-TT) as immunogens (Bidast et al., *Journal of Immunology*, 134: 457 (1985)). The immunization procedure involved a subcutaneous injection of 15 ug of beta-hCG in FCA as the initial dose into Balb/C mice, followed by a subcutaneous injection of 100 ug CTP-TT in Freund's incomplete adjuvant (FIA) eight months later. The cell fusion was performed on day 420. The animal was ; boosted on day 9 (subcutaneous) and day 3 (intraveneous) before cell fusion with injections of 15 ug beta-hCG.

Monoclonal antibody HT13 was produced by immunizing a Balb/C mouse subcutaneously with 10 ug hCG in FCA. Seven months later, the animal was boosted with 10 ug hCG subcutaneously in FIA on day 9, and with 10 ug intravenously on day 3 before fusion.

To produce monoclonal antibody AHT20 a Balb/C mouse was immunized subcutaneously with 15 ug of alpha-hCG in FIA. Six months later, the animal was injected subcutaneously with 15 ug of alpha-hCG in FIA. A third injection of 15 ug alpha-hCG was given intravenously six weeks later. Fusion was performed three days after this last immunization.

Screening of hybridoma cell culture supernatants for production of monoclonal antibodies to alpha- or beta-subunits, or hCG was done using a radioimmune assay as described by Bellet et al., (*Endocrinology*, 115: 330 (1984)). In brief, 100 ul of culture supernatant was incubated with 100 ul $^{125}$I-[alpha-hCG], $^{125}$I-[beta-hCG], or $^{125}$I-[hCG] (50,000 cpm) at 20° C. for 18 hours. The antigen-antibody complex was precipitated by 2 ml of 8% polyethylene glycol (PEG) (molecular weight 6,000) containing 1% goat antiserum (IgG and IgM heavy chain specific) for mouse immunoglobulins. Once antibody producing hybridomas were identified, they were cloned twice at limiting dilutions. Ascitic fluids were produced by intraperitoneal inoculation of Balb/C derived nude mice with $5 \times 10^5$ hybridoma cells. Ascitic fluids producing antibodies of interest were investigated for their specificity to $^{125}$I-[hCG], $^{125}$I-[alpha-hCG], $^{125}$[I]-beta-hCG, and $^{125}$I-[hLH]. The results of these binding studies are presented in Table I. Of the five monoclonal antibodies presented here, HT13 and FBT10 bind to all radiolabeled hormones. In addition, HT13 binds a determinant common to both alpha and beta-hCG subunits. However, C8 recognizes only $^{125}$I-[hCG], FBT11 recognizes only $^{125}$I-[beta-hCG], and AHT20 recognizes only free alpha-subunit.

characterization. Purification of these monoclonal antibodies from ascitic fluids was done using protein A Sepharose affinity chromatography. All of these antibodies were retained by the column at pH 8.0 and eluted at pH 5.0. The purified antibodies were then characterized with respect to their isotypes and affinity constants (Table II). The affinity constants of the monoclonal antibodies were determined by experiments using $^{125}$I-[alpha-hCG], $^{125}$I-[beta-hCG] or $^{125}$I-[hCG]. In brief, increasing amounts of unlabeled hormones were added to the reaction mixture containing purified monoclonal antibody diluted to a concentration which gives 50% of the maximal binding for either labeled hormone or subunit (Bellet et al., *Hybridoma*, 1: 218 (1982)). Evaluation of the binding data was performed according to Scatchard analysis (Scatchard, *Annals of the New York Academy of Sciences*, 51: 660 (1949)).

TABLE II

Physical Properties of Monoclonal Antibodies

| Clone | Isotype[a] | $K_a$[b] hCG | alpha-hCG | beta-hCG |
|---|---|---|---|---|
| C8 | IgG$_1$ | $0.90 \times 10^9$ | NT[c] | NT |
| FBT10 | IgG$_1$ | $0.25 \times 10^9$ | NT | $0.28 \times 10^9$ |
| FBT11 | IgG$_1$ | NT | NT | $0.47 \times 10^9$ |
| HT13 | IgG$_1$ | $3 \times 10^{10}$ | $1.3 \times 10^{10}$ | NT |
| AHT20 | IgG$_1$ | NT | $0.5 \times 10^9$ | NT |

[a]Isotype of each antibody was determined by RIA using rabbit antiserum specific for mouse immunoglobulin isotypes (IgG$_1$, IgG$_{2ab}$, IgG$_3$, IgM, IgA) as second antibody.
[b]Affinity constants measured for hCG, alpha-hCG, and beta-hCG by incubating monoclonal antibody with labeled $^{125}$-I[hCG], $^{125}$I-[alpha-hCG]or $^{125}$I-[beta-hCG] in the presence of increasing levels of unlabeled hormone or subunit. Ka values are expressed in liter per mole.
[c]Not tested.

B. Development of Monoclonal Radioimmune Assays

Various combinations of C8, FBT10, FBT11, AHT20, and HT13 on solid phase or as radiolabeled indicator antibodies were used to establish monoclonal RIAs specific for antigenic domains on hCG, alpha-subunit, and beta-hCG. In these procedures, polystyrene beads (outer diameter 0.64 cm, Precision Plastic Ball, Chicago, Ill.) were incubated overnight at 20° C. in the presence of antibody (ascitic fluids were diluted to 1:500 in 0.01 M phosphate buffer (pH 7.2) containing 0.15 M NaCl and 0.1% NaN3 (Pi/NaCl)). Antibody coated beads were washed three times with deionized water prior to use.

Protein A purified antibodies were radiolabeled with $^{125}$[I] by the Iodogen method (Fraker et al., *Biochemical and Biophysical Research Communications*, 80: 849 (1978)). Free iodine was removed by gel filtration on Sephadex G15 (Pharmacia) equilibrated with Pi/NaCl containing 1% bovine serum albumin. Specific activities

TABLE I

Specificity Testing of Monoclonal Antibodies

| Immunogen | Animal # | Clone | Ascitic Fluid Dilution | $^{125}$I-hCG | $^{125}$I-alpha-hCG | $\frac{B - Bo}{Bt} \times 100$[a] $^{125}$I-beta-hCG | $^{125}$I-hLH |
|---|---|---|---|---|---|---|---|
| hCG | 1 | C8 | 1:1000 | 43 | <1 | <1 | <1 |
| hCG | 2 | HT13 | 1:1000 | 49 | 80 | 49 | 25 |
| alpha-hCG | 3 | AHT20 | 1:1000 | <1 | 52 | <1 | <1 |
| beta-hCG and | | FBT10 | 1:1000 | 56 | <1 | 42.5 | 40 |
| CTP | 4 | FBT11 | 1:1000 | 1 | <1 | 54 | <1 |

[a]Binding values were obtained by RIA. Diluted ascitic fluids were incubated overnight with $^{125}$I-labeled hormone or subunit. Antigen-antibody complexes were precipitated with PEG as described and radioactivity bound in the complex was measured in gamma well counter. B denotes radioactivity bound in specific immune complex, Bo the radioactivity bound with a non-relevant monoclonal antibody and Bt the total radioactivity added to each assay. All binding values were determined in triplicate.

Monoclonal antibodies FBT10, C8, FBT11, AHT20 and HT13 were selected for further purification and range from 10–14 uCi/ug. Purified hormones or their free subunits were diluted in fetal calf sera to obtain various concentrations of assay standards.

"Simultaneous" and "forward" sandwich RIAs were used to examine the various immunoassay configurations.

In the "simultaneous" sandwich RIA, 100 ul of experimental sample and 100 ul of $^{125}$[I] antibody (200,000 cpm) diluted in Pi/NaCl were incubated at the same time with antibody-coated beads for 4 hours at 20° C. The beads were then washed three times with deionized water and the bound radioactivity measured in a gamma well counter. Positive binding values were calculated as S/N (signal/noise) greater than 2.5 as measured by dividing the cpms bound by various hormone standards by the cpms bound by fetal calf serum alone.

"Forward" sandwich RIAs for hCG and beta-hCG were also established. Beads coated with C8 or HT13 were used for the detection of hCG and FBTll coated beads were employed for measurement of free beta-hCG subunit. In the "forward" sandwich design, 200 ul of sample was incubated with antibody coated beads for 2 hours at 20° C. Beads were extensively washed with deionized water, followed by the addition of 200 ul of $^{125}$[I]- FBT10 (100,000 cpm in Pi/NaCl containing 10% fetal bovine sera and 40 ug/100 ul of a non-specific purified mouse IgG$_{2a}$). The reaction mixture was incubated for 1 hour at 20° C. followed by a washing step and the bound radioactivity determined.

Previous studies using high affinity monoclonal antibodies directed against soluble proteins had suggested a "simultaneous" sandwich assay configuration was the most sensitive for the detection of the protein in biological fluids (Wands et al., *Lancet, II:* 977 (1982); Ehrlich et al., *Science,* 221: 279 (1983)). In the case of alpha and beta-hCG subunits and intact hCG, the major problem is to detect low concentrations of subunit in the presence of high concentrations of intact hCG. This is particularly true during normal pregnancy and during tumorigenesis where beta-hCG subunit levels may be present in the blood in nanogram quantities, while intact hCG may be present in microgram quantities (Cole et al., *Journal of Clinical Endocrinology and Metabolism,* 58: 1200 (1984)). This observation has to be taken into account even assuming the immunoassays are entirely specific for beta-hCG and hCG. Therefore, the first assays established for beta-hCG using antibodies FBT10 and FBT11 studied their performance in a "simultaneous" sandwich mode. In an experiment where FBT11 (specific for beta-hCG) was linked to a solid phase support and FBT10 (reacts equally with both beta-hCG and hCG) served as the radiolabeled indicator probe a sensitive assay (<0.4 ng/ml) was developed using the "simultaneous" sandwich configuration. However, when attempts were made to measure the levels (1–10 ng/ml) of beta-hCG in serum in the presence of 10 ug/ml of hCG, a concentration commonly found in serum during normal pregnancy (Braustein et al., *American Journal of Obstetrics and Gynecology,* 126: 678 (1976)), a false negative result was observed. If, for example, the experiment was performed in reverse and FBT10 was the capture antibody on the solid support and FBTll the radio-labeled indicator probe, identical results were obtained. Thus, in the commonly observed physiologic condition where low levels of beta-hCG coexist with hCG, it is not possible to use the "simultaneous" sandwich assay design presented here to detect beta-hCG. The false negative results are most likely due to binding of the FBT10 probe to high concentrations of hCG in the solid phase making it unavailable for binding to and detection of beta-hCG linked through FBT11 to the solid phase support. As determined in the second experiment, high levels of hCG also bind all of the available FBT10 antibody coupled to the solid phase support, leaving little, if any, antibody to bind to soluble free beta-hCG subunit.

In order to circumvent the problem of false negative results, the assay configuration for beta-hCG was changed to a "forward" sandwich design. Based on previous studies described above, it was important to select the correct capture antibody to be linked to the solid phase support, thus, in order to avoid a block in beta-hCG binding to the bead, FBT11 was used on the solid phase since FBT10 binding to beta-hCG was blocked when high concentrations of hCG were present in serum (data not shown). The "forward" sandwich assay design requires an initial incubation of solid phase support with the native hormone or subunit diluted in serum followed by a washing step to remove any excess non-bound hormone. Next, the radiolabeled indicator antibody is added followed by a washing step. The "forward" sandwich assay for beta-hCG subunit was sensitive to a concentration of 0.1 ng/ml.

Experiments were also done to study the effect of increasing concentrations of hCG on the measurement of free beta-hCG subunit in this assay configuration. The addition of 100 ng/ml of hCG to the beta-hCG assay standards had no effect on the accurate measurement of beta-hCG in serum. However, as the concentration of hCG was progressively increased to 10,000 mg/ml, the inventors observed enhanced binding for beta-hCG in the FBT11-FBT10 assay leading to a false positive result. This same phenomenon was observed in the C8-FBT10 "forward" sandwich assay for hCG performed under identical conditions. In other words, at a very high concentration of beta-hCG (1,000 ng/ml), a false positive result was observed for detection of hCG. These findings may be explained in part by either a cross-reactivity of FBT11 not observed in the initial specificity testing (Table I) with epitopes on hCG or the presence of beta-hCG or beta-hCG "like" impurities in the hCG standard preparation. Similarly, it was also possible that C8 may not be totally specific for hCG and detect a cross-reactive substance in the purified beta-hCG hormone standard.

Experiments were performed to examine the specificity of the C8-FBT10 and FBT11-FBT10 assays for hCG and free beta-hCG subunit, respectively, by determining the relative immunoreactivities of various other glycoprotein hormones and their subunits. It is noteworthy that at physiologic concentrations (Vaitukaitis et al., *Recent Progress in Hormone Research,* 32: 289 (1976)) none of the glycoprotein hormones or their subunits demonstrated substantial cross-reactivity with beta-hCG in the FBT11-FBT10 immunoassay, except the hCG hormone standard (Table III). However, there was immunoreactivity at very high concentrations of alpha-hCG and beta-hLH in the FBT11-FBT10 immunoassay. Similarly, with the C8-FBT10 assay for hCG a significant binding reactivity was observed with alpha-hCG (1.9%, Table III). The relative cross-reactivities of the remaining glycoprotein hormones and their subunits were below 1%. These findings are consistent either with a partial cross-reactivity of the FBTll and C8 antibodies with similar epitopes on other glycoprotein hormones and subunits or, alternatively, the presence of glycoprotein hormone contamination in the purified assay standards.

shared FBT11 and C8 epitopes on other glycoprotein hormones and their subunits, but was due to the pres-

TABLE III

| System | Relative Immunoreactivities of Glycoprotein Hormones and Their Subunits | | | | | | | | |
|---|---|---|---|---|---|---|---|---|---|
| | hCG | hLH | hFSH | hTSH | alpha-hCG | beta-hCG | beta-hLH | beta-hFSH | beta-hTSH |
| C8 + FBT10[a] | 100 | 0.40 | 0.58 | 0 | 1.90 | 0.50 | 0.16 | 0 | 0 |
| FBT11 + FBT10[b] | 0.77 | 0.04 | 0.05 | 0.005 | 0.14 | 100 | 0.20 | 0.005 | 0.009 |
| AHT20 + HT13[c] | 0.02 | 2.2 | 0.44 | 0.29 | 100 | 0.04 | NT[d] | NT | NT |

[a] This assay is specific for hCG. S/N values obtained by hCG standards were compared with those obtained using other glycoprotein hormones or subunits.
[b] This assay is specific for free beta-hCG, data from beta-hCG standards were compared to those from other glycoprotein hormones or subunits.
[c] This assay is specific for free alpha-subunit, data from alpha-hCG standards were compared to those from other glycoprotein hormones or subunits.
[d] Not tested.

C. Analysis of Glycoprotein Hormone Standards

Purified standard hCG and its subunits were analyzed by 10% and 12.5% SDS-PAGE. Samples were diluted in 0.1% SDS buffer with or without dithiothreitol (DTT). Standard molecular weight markers (Biorad) were used to estimate molecular weights of the hormone standards. Samples with DTT were boiled at 100° C. for 2 minutes before application to the gels. After electrophoresis, proteins were visualized on the gel by either comassie blue or silver staining (Biorad) techniques. In some experiments, hCG and its subunits were applied to gels in duplicate. One portion of the gel was subjected to protein staining and the other portion was used for analysis in the monoclonal RIAs. For this procedure, the wet gels were cut into 1.7 mm fractions using a gel slicer. The proteins were eluted from the gel fractions by shaking overnight at 4° C. with 0.5 ml of Pi/NaCl. The eluates were analyzed for hCG and beta-hCG subunit binding activity by monoclonal RIAs following dilution in fetal bovine serum.

SDS-PAGE analysis was done on the hCG, alpha-hCG, and beta-hCG standards. Using this technique, a single protein band for hCG was observed. In addition, the alpha-hCG and beta-hCG hormone standards migrated as a single band. When assessed under reducing conditions hCG was dissociated into its alpha and beta subunits. Little, if any, cross contamination with other glycoprotein hormones was evident by this technique.

Further experiments were performed with the hCG standard following gel electrophoresis under non-reducing conditions in which the gel was sliced and eluted with Pi/NaCl. Each eluant fraction was assessed for the presence of beta-hCG by the FBT11-FBT10 immunoassay and hCG by the C8-FBT10 immunoassay. Two immunoreactive peaks were present. The C8-FBT10 assay detects native hCG. The second peak reacted only in the FBT11-FBT10 RIA for beta-hCG. Where there was immunoreactivity with both assays, there was co-migration with the hCG and beta-hCG hormone standards, respectively. Thus, the "purified" hCG standard was contaminated with beta-hCG subunit. This contamination was only detected by the beta-hCG FBT11-FBT10 immunoassay. As shown by these experiments, there was no cross-reactivity between C8 and beta-hCG or between FBT11 and hCG. Thus, there are unique epitopic specific domains recognized by FBT11 on beta-hCG and by C8 on hCG.

Since the alpha-hCG hormone standard appeared to give some cross-reactivity (Table III) in the C8-FBT10 assay for hCG, an identical experiment to that outlined above was performed. Following gel electrophoresis of the alpha-hCG standard, hCG and beta-hCG contaminants were identified. This data shows that the relative cross-reactivity depicted in Table III was not due to ence of contamination in the glycoprotein hormone standards.

D. Isolation and Characterization of beta-hCG Present in the hCG Hormone Standard Affinity chromatography was done using monoclonal antibody FBT11. Ascitic fluid containing FBT11 was coupled to CNBr-activated Sepharose 4B (Pharmacia) as described in Wands et al. (*Proceedings of the National Academy of Sciences, USA*, 79: 1277 (1982)). To block unreactive sites, the gel was incubated for 2 hours in 0.1 M Tris buffer (pH 8.0). The gel was then sequentially washed on a sintered-glass funnel with large volumes of 0.1 M acetate buffer (pH 4.0) and 0.1 M Tris buffer (pH 8.0) both containing 0.5 M NaCl. FBT11 covalently coupled to Sepharose 4B was finally suspended in Pi/NaCl and stored at 4° C. Small columns of FBT11 coupled Sepharose were prepared in 5 ml syringes and equilibrated with 0.1 M ammonium bicarbonate buffer (pH 8.0). Samples containing hCG or beta-hCG subunit in Pi/NaCl were applied to the column. The hormones were incubated with the column at 4° C. for 2 hours. Non-absorbed material was removed by extensive washing with ammonium bicarbonate buffer. The column was then washed with 15 ml of deionized water. Bound material was subsequently eluted with 2.5% (v/v) acetic acid. Eluates were immediately frozen in acetone/dry ice and lyophilized. The lyophilization products were dissolved in Pi/NaCl and stored at −20° C. prior to analysis.

In affinity chromatographic profiles of hCG and beta-hCG, when applied as a mixture on the FBT11 Sepharose column, hCG was not bound by the column, but eluted at pH 7.2. In contrast, beta-hCG was completely bound to the column under these conditions and was recovered (80%) following elution at pH 3.0.

This approach was used to further characterize the beta-hCG impurity in the hCG hormone standard as previously described. In this experiment, SDS-PAGE analysis was performed before and after FBT11 affinity chromatography of hCG and the subsequent measurement of immunoreactivity of the eluted fractions in the FBT11-FBT10 and C8-FBT10 immunoassays were combined.

These studies showed that the beta-hCG component was present in the hCG standard before affinity chromatography. Following affinity chromatography on the FBT11 column, the unretained fraction contained only hCG and the beta-hCG contaminant was bound to the solid phase support. The final proof of the presence of the beta-hCG contaminant was by the elution and recovery of beta-hCG from the FBT11 affinity column at pH 3.0.

EXAMPLE 2

Detection of Free Alpha-hCG Subunit in the Presence of hCG Standard

An experiment was done to determine the effect of increasing concentrations of hCG standard on the detection of free alpha-hCG subunit using the AHT20-HT13 sandwich immunoassay. This assay was performed analogously to those described above, except AHT20, which is specific for free alpha-hCG subunit, was bound to the polystyrene bead and $^{125}$I-HT13 was used to detect the presence of bound free alpha-hCG subunit. Purified alpha-hCG subunit (1, 5, 10 and 20 ng/ml) was measured in the presence of 0, $10^2$, $10^3$ and $10^4$ ng/ml hCG standard. The results of this experiment are shown in Table IV.

No difference was seen between the level of free alpha-hCG subunit detected in the absence of hCG and when hCG was present at $10^2$ ng/ml. However, at higher concentrations of hCG standard ($10^3$ and $10^4$ ng/ml), enhanced binding occurred in the free alpha-hCG specific binding assay. This enhanced binding shows that the hCG standard is contaminated with free alpha-hCG subunit.

TABLE IV

Detection of Free alpha-hCG Subunit in the Presence of hCG Standard

| [Free alpha-hCG subunit][a] | Free alpha-hCG subunit | $S/N$[b] hCG Standard[a] | | |
|---|---|---|---|---|
| | | $10^2$ | $10^3$ | $10^4$ |
| 0.0 | 1 | 2 | 10 | 32 |
| 1.0 | 6 | 6 | 22 | 35 |
| 5.0 | 22 | 24 | 30 | 36 |
| 10.0 | 34 | 34 | 34 | 38 |
| 20.0 | 37 | 36 | 36 | 36 |

[a]ng/ml
[b]signal-to-noise ratio

EXAMPLE 3

Detection of Free beta-hCG Subunit in Serum of Patients with Normal Pregnancy and Choriocarcinoma The levels of free beta-hCG subunit was determined in serum of a patient in the twelfth week of pregnancy and in the serum of a patient with choriocarcinoma (Table V). The assay was performed using a bead coated with FBT11 (specific for free beta-hCG subunit) and $^{125}$I-FBT10 (reactive with both free beta-hCG subunit and hCG). This data shows that the sample from the choriocarcinoma patient had significantly higher levels of free beta-hCG subunit in the serum than was present in the serum of a patient with normal pregnancy.

TABLE V

Measurement of free beta-hCG Subunit Serum Levels in the Presence of High Concentrations of hCG in Normal Pregnancy and Choriocarcinoma[a]

| Serum Dilution | Pregnancy[b] cpm bound (ng/ml beta-hCG)[c] | Choriocarcinoma[b] cpm bound (ng/ml beta-hCG)[c] |
|---|---|---|
| Undiluted | 14,800 (>20) | 13,670 (>20) |
| 1:10 | 4,256 (83) | 13,500 (>200) |
| 1:100 | 420 (80) | 14,500 (>2000) |
| 1:1000 | 160 | 2,664 (3234) |

[a]Forward assay using 200 ul of sample first incubated with FBT11 coated bead (2 h). The second incubation was performed in the presence of FBT11 coated bead and $^{125}$I-FBT10 (100,000 cpm) (1 h). Total incubation time was 3 h.
[b]Levels of hCG as measured by specific assay were 37,000 ng/ml for pregnancy and 40,000 ng/ml for choriocarcinoma.
[c]As determined by the standard curve.

EXAMPLE 4

Levels of Free beta-hCG Subunit and hCG in Normal Pregnancy and Choriocarcinoma Levels of free beta-hCG subunit and hCG were determined in serum taken at various times during gestational development in normal pregnancy and in serum of patients with choriocarcinoma.

Free beta-hCG subunit was detected by incubating hours. After washing, 200 ul of $^{125}$I-FBT10 (100,000 cpm) was added to the bead and allowed to incubate for an additional hour. At the end of this time, the bead was washed again and the total counts bound to the bead determined using a gamma counter.

Levels of hCG were determined using the same procedure as described above except that the bead was coated with C8.

Figure 2:
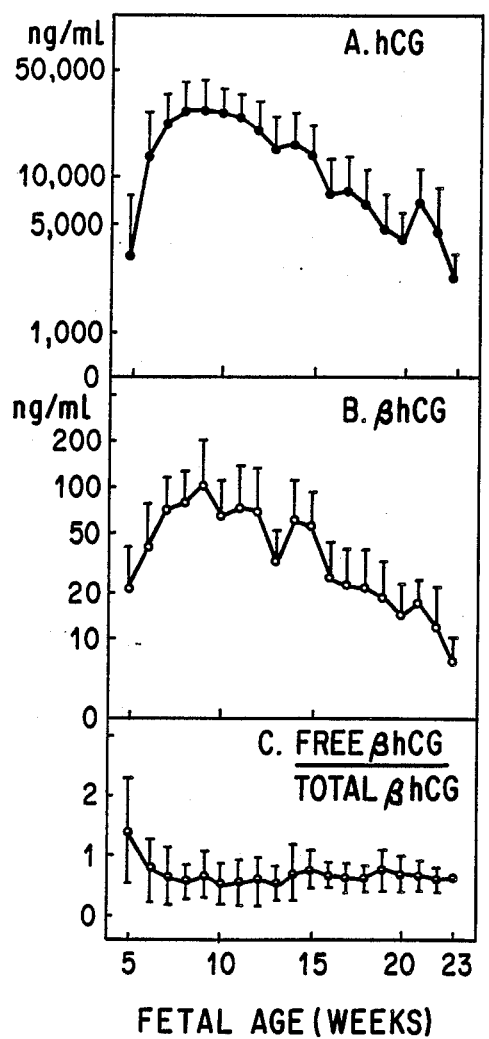
FIG. 2: Levels of hCG (A) and free beta-hCG subunit (B) in normal pregnant serum during gestation. Free beta-hCG subunit was assayed by FBT11-FBT10 ( 0 --- 0 ) and hCG was assayed by C8-FBT10 ( ● --- ● ). (c) percent molar ratio

FIG. 2 shows the levels of serum beta-hCG subunit and hCG in normal pregnancy with increasing gestational age. There is a direct relationship between free beta-hCG subunit and hCG levels during pregnancy. More significantly, as shown in FIG. 2C, is the fact that the ratio of free beta-hCG subunit to hCG remains constant from week 5 to 23 of gestation. This phenomenon is particularly important when attempting to differentiate normal pregnancy from choriocarcinoma.

Figure 3:
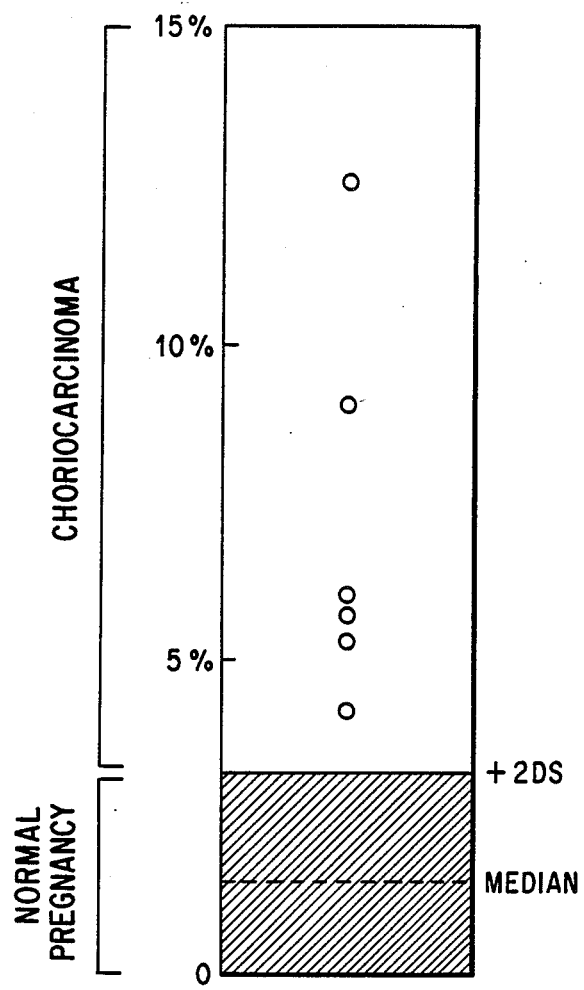
FIG. 3: Comparison of the ratio of free beta-hCG subunit to total B hCG in specimens from patients with choriocarcinoma compared to like ratios in normal pregnancy.

FIG. 3 shows the ratio of free beta-hCG subunit to total hCG in the serum of six patients with choriocarcinoma as compared to the ratio normally found in normal pregnancy. All six patients with choriocarcinoma had elevated ratios ranging from approximately 3–13% higher than the ratios commonly encountered during normal pregnancy. This ratio enables the differentiation of patients with choriocarcinoma or trophoblastic disease from patients with normal pregnancy.

EXAMPLE 5

Levels of Free beta-hCG Subunit and hCG in Various Human Tumors

Measurements were made of free beta-hCG subunit and hCG in serum samples derived from patients with various tumors. The assays were run as described above. Table VI shows the levels of hCG and Table VII shows the levels of free beta-hCG subunit present in the serum. The baseline serum levels of free beta-hCG subunit and hCG were established using samples from 366 patients with non-neoplastic disease such as hepatitis or cirrhosis (disease control). Based on these findings, levels of hCG <1 ng/ml and levels of free beta-hCG subunit <0.2 ng/ml would be considered normal. Based on this criteria, the immunoassays of the invention are highly accurate in detecting the presence of certain human tumors. This is especially so with respect to the samples from patients with treated testicular and trophoblastic tumors wherein all samples showed elevated levels of hCG and free beta-hCG subunit.

The presence of hCG in a female is indicative of either pregnancy, trophoblastic disease, or a nontrophoblastic malignant tumor. The presence of abnormal levels of free beta-hCG subunits suggests the development of either trophoblastic disease or a non-trophoblastic malignant tumor. To determine whether a specimen contains an abnormal level of free beta-hCG subunit, the value of free beta-hCG subunit obtained for a particular specimen is compared with usual values observed in either pregnant or apparently healthy individuals.

Clinical data indicates that an elevation in the ratio of the free beta-hCG subunit to hCG is found in patients with malignant tumors.

TABLE VI

| Serum Levels of hCG in Various Human Tumors | | | | | |
| --- | --- | --- | --- | --- | --- |
| Tumor | No. | <1 ng/ml | 1-5 ng/ml | 5-10 ng/ml | >10 ng/ml |
| Disease Control | 366 | 364 (99.5%) | 2 (0.5%) | — | — |
| Hepatoma | 76 | 66 (87%) | 10 (13%) | — | — |
| Colon and Rectum | 12 | 12 (100%) | — | — | — |
| Pancreas | 10 | 10 (100%) | — | — | — |
| Esophagus | 8 | 8 (100%) | — | — | — |
| Stomach | 12 | 12 (100%) | — | — | — |
| Breast | 14 | 14 (100%) | — | — | — |
| Ovarian | 32 | 32 (100%) | — | — | — |
| Prostate | 3 | 3 (100%) | — | — | — |
| Cervix | 4 | 4 (100%) | — | — | — |
| Testicular (treated) | 10 | — | — | — | 10 (100%) |
| Trophoblastic (treated) | 18 | — | 1 (5.5%) | 1 (5.5%) | 16 (89%) |

TABLE VII

| Serum Levels of Free beta-hCG Subunit in Various Human Tumors | | | | | |
| --- | --- | --- | --- | --- | --- |
| Tumor | No. | <0.2 ng/ml | 0.2-1 ng/ml | 1-10 ng/ml | >10 ng/ml |
| Disease Control | 366 | 362 (98.9%) | 3 (0.8%) | 1 (0.3%) | — |
| Hepatoma | 76 | 63 (82.9%) | 11 (14.5%) | — | 2 (2.6%) |
| Colon and Rectum | 12 | 12 (100%) | — | — | — |
| Pancreas | 10 | 7 (70%) | 2 (20%) | — | 1 (10%) |
| Esophagus | 8 | 8 (100%) | — | — | — |
| Stomach | 12 | 12 (100%) | — | — | — |
| Breast | 14 | 14 (100%) | — | — | — |
| Ovarian | 32 | 31 (96%) | 1 (4%) | — | — |
| Prostate | 3 | 3 (100%) | — | — | — |
| Cervix | 4 | 4 (100%) | — | — | — |
| Testicular (treated) | 10 | — | — | 4 (40%) | 6 (60%) |
| Trophoblastic (treated) | 18 | — | 2 (11%) | 2 (11%) | 14 (78%) |

Having now fully described this invention, it will be readily apparent that the same can be performed within a wide and equivalent range of parameters, conditions and the like, without affecting the spirit or scope of the invention or any embodiment thereof.

What is claimed as new and desired to be covered by letters patent is:

1. A method for the determination of a free protein subunit of hCG in a sample containing intact quaternary hCG, which comprises:
    (a) contacting said sample with a first monoclonal antibody which is bound to a carrier, wherein said first monoclonal antibody binds epitopic determinants bindable only on said free protein subunit;
    (b) incubating the components of step (a) for a period of time and under conditions sufficient to form an immune complex between said free protein subunit, said first monoclonal antibody, and said carrier;
    (c) separating said carrier of step (b) from said sample;
    (d) adding to said carrier of step (c), a detectably labeled second monoclonal antibody, wherein said second monoclonal antibody binds epitopic determinants bindable on both said free protein subunit and said intact quaternary hCG;
    (e) separating said carrier of step (d) from the liquid phase; and
    (f) determining the detectably labeled second monoclonal antibody in said carrier or in said liquid phase, which is a measure of the amount of said free protein subunit in said sample.

2. A method for the determination of a free protein subunit of hCG in a sample containing intact quaternary hCG, which comprises:
    (a) contacting said sample with a first monoclonal antibody which will be bound to a carrier, wherein said first monoclonal antibody binds epitopic determinants bindable only on said free protein subunit;
    (b) providing a carrier which is capable of binding said first monoclonal antibody;
    (c) incubating the components of steps (a) and (b) for a period of time and under conditions sufficient to form an immune complex between said free protein subunit, said first monoclonal antibody, and said carrier;
    (d) separating said carrier of step (c) from said sample;
    (e) adding to said carrier of step (d) a detectably labeled second monoclonal antibody, wherein said second monoclonal antibody binds epitopic determinants bindable on both said free protein subunit and said intact quaternary hCG;
    (f) separating said carrier of step (e) from the liquid phase; and
    (g) determining the detectably labeled second monoclonal antibody in said carrier or in said liquid phase, which is a measure of the amount of said free protein subunit in said sample.

3. A method for the determination of free beta-hCG subunit in a sample, which comprises:

(a) contacting said sample with monoclonal antibody FBT11; and
(b) detecting the antibody-free beta-hCG subunit complex.

4. A method for the determination of free alpha-hCG subunit in a sample, which comprises:
(a) contacting said sample with monoclonal antibody AHT20; and
(b) detecting the antibody-free alpha-hCG subunit complex.

5. A method for the determination of hCG in a sample, which comprises:
(a) contacting said sample with the monoclonal antibody; and
(b) detecting the antibody-hCG subunit complex.

6. A method for determining the ratio of free protein subunit of hCG to intact quaternary hCG containing said subunit in a sample, which comprises:
(a) determining the amount of free protein subunit present in said sample according to the method of claim 1;
(b) determining the amount of intact quaternary hCG containing said subunit in said sample; and
(c) dividing the value obtained in step (a) by the value obtained in step (b).

7. The method of claim 6, wherein said step (b) comprises:
(b1) contacting said sample with a first monoclonal antibody which is bound to a carrier, wherein said first monoclonal antibody binds epitopic determinants bindable on said intact quaternary hCG;
(b2) incubating the components of step (b1) for a period of time and under conditions sufficient to form an immune complex between said intact quaternary hCG, said first monoclonal antibody, and said carrier;
(b3) separating said carrier of step (b2) from said sample;
(b4) adding to said carrier of step (b3), a detectably labeled second monoclonal antibody, wherein said second monoclonal antibody binds epitopic determinants bindable on said intact quaternary hCG;
(b5) separating said carrier of step (b4) from the liquid phase; and
(b6) determining the detectably labeled second monoclonal antibody in said carrier or in said liquid phase, which is a measure of the amount of said intact quaternary hCG in said sample.

8. The method of claim 7 wherein said first monoclonal antibody and said second monoclonal antibody is the monoclonal antibody HT-13.

9. A method for determining the ratio of free protein subunit of hCG to intact quaternary hCG containing said subunit in a sample, which comprises:
(a) determining the amount of free protein subunit present in said sample according to the method of claim 2;
(b) determining the amount of intact quaternary hCG containing said subunit in said sample; and
(c) dividing the value obtained in step (c) by the value obtained in step (b).

10. The method of claim 9, wherein said step (b) comprises:
(b1) contacting said sample with a first monoclonal antibody which will be bound to a carrier, wherein said first monoclonal antibody binds epitopic determinants bindable on said intact quaternary hCG;
(b2) providing a carrier which is capable of binding said first monoclonal antibody;
(b3) incubating the components of steps (b1) and (b2) for a period of time under conditions sufficient to form an immune complex between said intact quaternary hCG, said first monoclonal antibody, and said carrier;
(b4) separating said carrier of step (b3) from said sample
(b5) adding to said carrier of step (b4), a detectably labeled second monoclonal antibody, wherein said second monoclonal antibody binds epitopic determinants bindable on said intact quaternary hCG;
(b6) separating said carrier of step (b5) from the liquid phase; and
(b7) determining the detectably labeled second monoclonal antibody in said carrier or in said liquid phase, which is a measure of the amount of said intact quaternary hCG in said sample.

11. The method of claims 1 or 2 wherein said first monoclonal antibody is the monoclonal antibody FBT11 and said second monoclonal antibody is the monoclonal antibody selected from the group consisting of FBT10 and HT13.

12. The method of claims 1 or 2 wherein said first monoclonal antibody is the monoclonal antibody AHT20 and said second monoclonal antibody is the monoclonal antibody HT13.

13. The method of claims 1, 6, 7, 2, 9 or 44 wherein said free protein subunit is alpha-hCG.

14. The method of claims 1, 6, 7, 2, 9 or 44 wherein said free protein subunit is beta-hCG.

15. The method of claims 7 or 10 wherein said first monoclonal antibody is the monoclonal antibody FBT10 and said second monoclonal antibody is the monoclonal antibody HT13.

16. The method of claims 7 or 10 wherein said first monoclonal antibody is the monoclonal antibody HT13 and said second monoclonal antibody is the monoclonal antibody FBT10.

17. The method of claim 3 wherein said monoclonal antibody is detectably labeled.

18. The method of claim 3 which in step (b) further comprises:
(a) contacting said free beta-hCG subunit with a monoclonal antibody selected from the group consisting of FBT10 and HT13.

19. The method of claim 18 wherein one or more of said monoclonal antibodies is detectably labeled.

20. The method of claim 4 wherein said monoclonal antibody is detectably labeled.

21. The method of claim 4 which in step (b) further comprises
(a) contacting said free alpha-hCG subunit with the monoclonal antibody HT13.

22. The method of claim 21 wherein one or more of said monoclonal antibodies is detectably labeled.

23. The method of claim 5 wherein said monoclonal antibody is detectably labeled.

24. The method of claim 5 which in step (b) further comprises
(a) contacting said hCG with a monoclonal antibody selected from the group consisting of FBT10 and HT13.

25. The method of claim 24 wherein one or more of said monoclonal antibodies is detectably labeled.

26. The method of claims 1, 3, 6, 7, 17, 20, 23, 19, 22, 35, 36, 37, 25, 2, 9, 10 or 44 wherein said detectable label is selected from the group consisting of an enzyme, a radioactive isotope, a fluorescent compound, a chemiluminescent compound and a bioluminescent compound.

27. A kit useful for the detection of a first free protein subunit of hCG in a sample containing intact quaternary hCG, comprising a carrier being compartmentalized to receive in close confinement therein one or more containers comprising:
(a) a first container comprising a first monoclonal antibody, wherein said first monoclonal antibody binds epitopic determinants bindable only on said first free protein subunit; and
(b) a second container comprising a detectably labeled second monoclonal antibody, wherein said second monoclonal antibody binds epitopic determinants bindable on both said first free protein subunit and said intact quaternary hCG.

28. The kit of claim 27 wherein said first monoclonal antibody is the monoclonal antibody FBT11 and said second monoclonal antibody is the monoclonal antibody selected from the group consisting of FBT10 and HT13.

29. A kit useful for the detection of a first and second free protein subunit of hCG in a sample containing intact quaternary hCG, comprising a carrier being compartmentalized to receive in close confinement therein one or more containers comprising:
(a) a first container comprising a first monoclonal antibody, wherein said first monoclonal antibody binds epitopic determinants bindable only on said first free protein subunit;
(b) a second container comprising a detectably labeled second monoclonal antibody, wherein said second monoclonal antibody binds epitopic determinants bindable on both said first free protein subunit and said intact quaternary hCG;
(c) a third container comprising a third monoclonal antibody, wherein said third monoclonal antibody binds epitopic determinants bindable only on said second free protein subunit; and
(d) a fourth container comprising a fourth monoclonal antibody, wherein said fourth monoclonal antibody binds to epitopic determinants bindable on both said second free protein subunit and said intact quaternary hCG.

30. The kit of claim 29 which further comprises a fifth container which comprises a fifth monoclonal antibody, wherein said fifth monoclonal antibody binds to epitopic determinants bindable only on said intact quaternary hCG.

31. The kit of claim 29 wherein said third monoclonal antibody is the antibody AHT20 and said fourth monoclonal antibody is the monoclonal antibody HT13.

32. A monoclonal antibody selected from the group consisting of monoclonal antibodies FBT10, FBT11, AHT20 and HT13.

33. A continuous hybridoma cell line selected from the group consisting of I-488, I-499, I-490 and I-491.

34. A monoclonal antibody produced by any of the hybridoma cell lines of claim 33.

* * * * *